(12) United States Patent
Krause

(10) Patent No.: US 9,956,045 B2
(45) Date of Patent: May 1, 2018

(54) CANNULATED INSTRUMENT FLUSHING AND CLEANING INSTRUMENT

(71) Applicant: William R. Krause, Charlottesville, VA (US)

(72) Inventor: William R. Krause, Charlottesville, VA (US)

( * ) Notice: Subject to any disclaimer, the term of this patent is extended or adjusted under 35 U.S.C. 154(b) by 92 days.

(21) Appl. No.: 14/645,384

(22) Filed: Mar. 11, 2015

(65) Prior Publication Data
US 2015/0305819 A1    Oct. 29, 2015

Related U.S. Application Data

(60) Provisional application No. 61/951,430, filed on Mar. 11, 2014.

(51) Int. Cl.
*A61B 19/00*     (2006.01)
*A61B 90/70*     (2016.01)

(52) U.S. Cl.
CPC .............. *A61B 19/34* (2013.01); *A61B 90/70* (2016.02); *A61B 2090/701* (2016.02)

(58) Field of Classification Search
CPC .... A61B 90/70; A61B 19/34; A61B 2090/701
See application file for complete search history.

(56) References Cited

U.S. PATENT DOCUMENTS

| | | | |
|---|---|---|---|
| 5,090,433 A | 2/1992 | Kamaga | |
| 5,168,593 A * | 12/1992 | Poje | A46B 3/18 15/104.2 |
| 5,240,675 A * | 8/1993 | Wilk | A61B 1/122 15/104.05 |
| 5,279,317 A | 1/1994 | Bowman | |
| 5,425,815 A | 6/1995 | Parker et al. | |
| 5,488,761 A | 2/1996 | Leone | |
| 5,658,273 A * | 8/1997 | Long | A61B 17/3417 606/1 |
| 6,047,431 A * | 4/2000 | Canonica | B08B 9/045 15/104.095 |

(Continued)

FOREIGN PATENT DOCUMENTS

| | | |
|---|---|---|
| DE | 10125521 A1 | 5/2001 |
| DE | 102010008745 A1 | 2/2010 |

*Primary Examiner* — Michael Barr
*Assistant Examiner* — Benjamin L Osterhout
(74) *Attorney, Agent, or Firm* — Kimberly O Snead, Esq

(57) ABSTRACT

An apparatus for cleaning cannulated surgical tools comprises a hollow body with lavage fluid holes and a brush adaptor at a first end and an inlet adaptor affixed to a second end. A body hub, consisting of inlet channel and drain channel is in liquid communication with an inner lavage fluid tube. A lavage connection tube is in liquid communication with the hollow body at the brush adaptor and through the upper connecting lavage fluid orifice. An inner lavage fluid tube, having an inner channel, extends within the hollow body with a distal end in liquid communication with the inner channel within the inlet adaptor. There are multiple spray openings proximate the distal end of the inner lavage fluid connection tube and a tube brush is dimensioned to fit within the inner channel. The apparatus can be combined with a reservoir to make the unit self-contained.

20 Claims, 20 Drawing Sheets

(56) References Cited

U.S. PATENT DOCUMENTS

| | | | |
|---|---|---|---|
| 6,699,331 B1 * | 3/2004 | Kritzler | A61B 17/221 |
| | | | 134/22.11 |
| 6,920,662 B2 | 7/2005 | Moore | |
| 7,979,943 B2 * | 7/2011 | Arai | A61B 1/122 |
| | | | 15/104.05 |
| 2003/0000035 A1 | 1/2003 | Tomooka et al. | |
| 2003/0213501 A1 | 11/2003 | Thomson et al. | |
| 2004/0031112 A1 | 2/2004 | Saurer | |
| 2004/0255414 A1 | 12/2004 | Tulipana | |
| 2008/0188715 A1 * | 8/2008 | Fujimoto | A61B 1/00091 |
| | | | 600/157 |
| 2009/0119856 A1 | 5/2009 | Onishi | |
| 2011/0005012 A1 | 12/2011 | Le Blanc | |

* cited by examiner

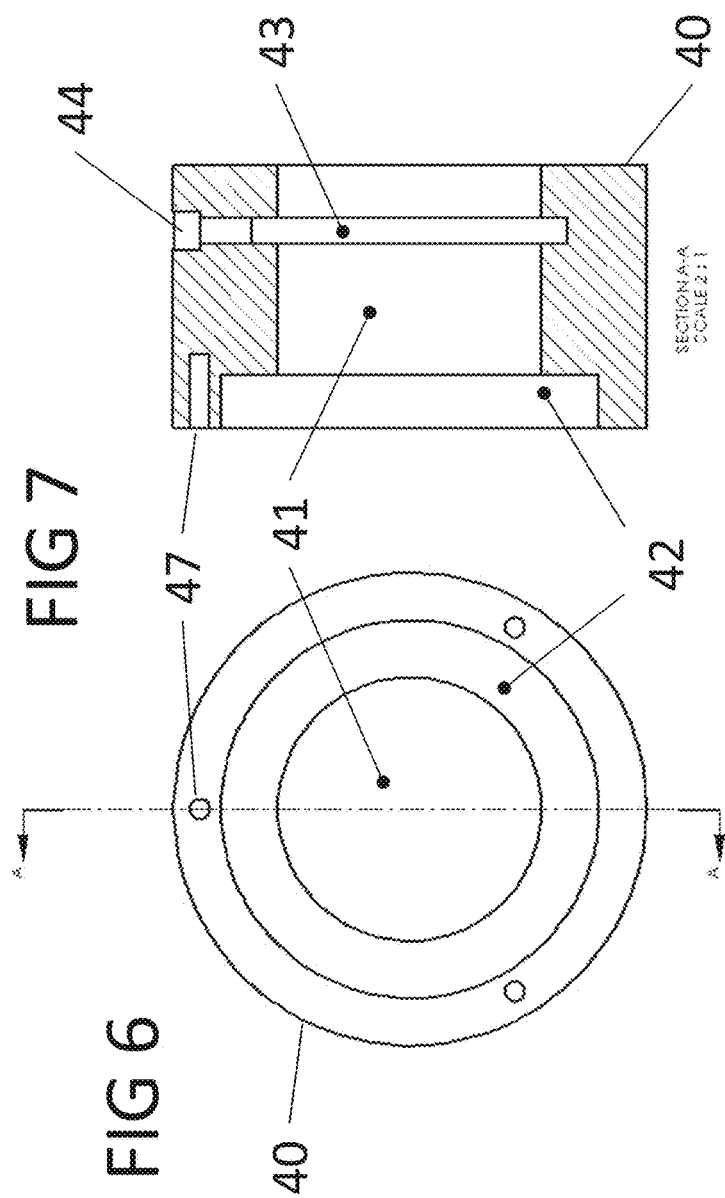

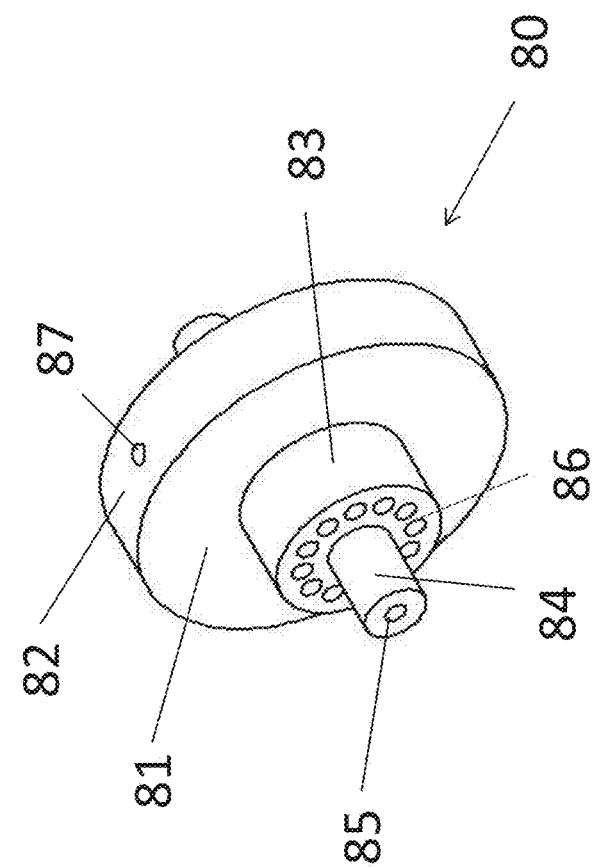

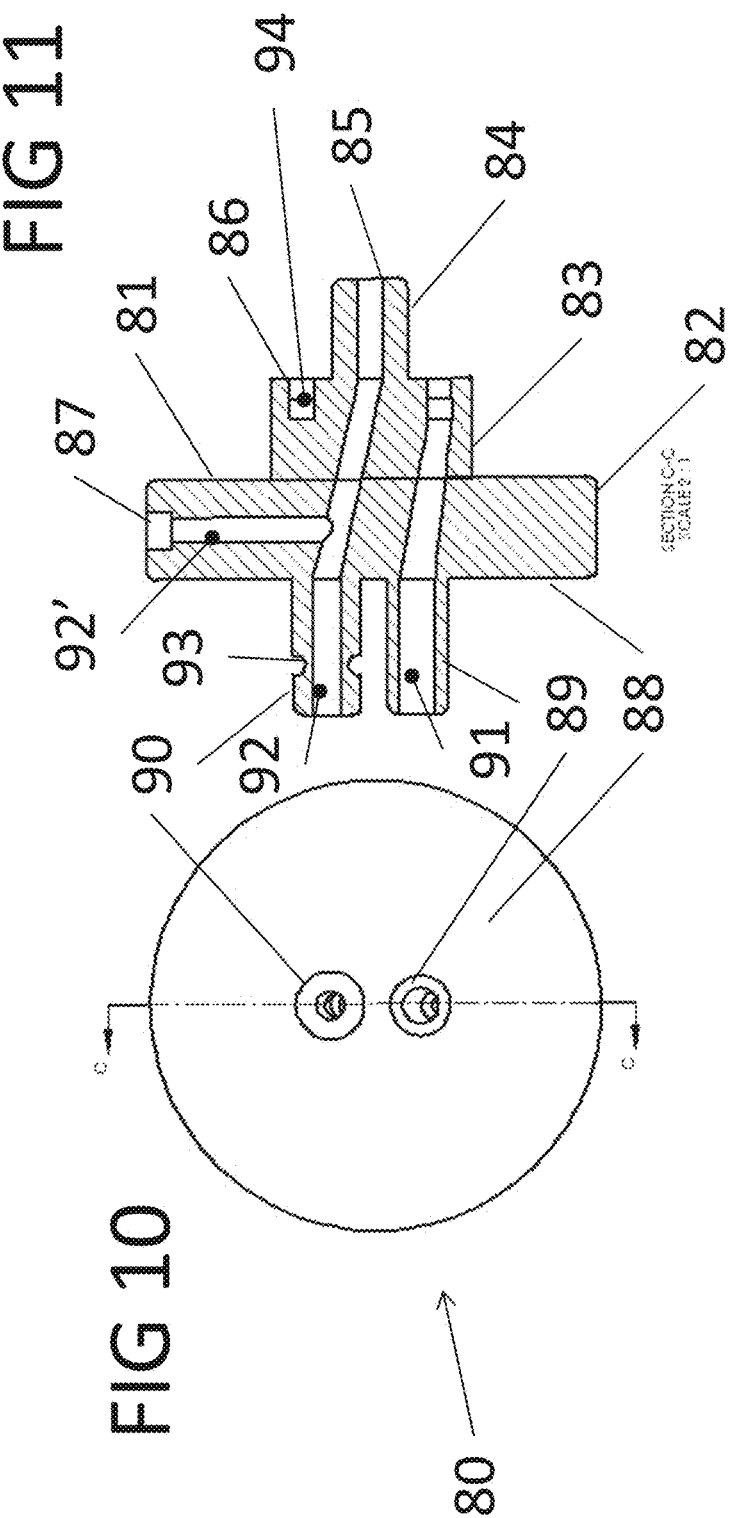

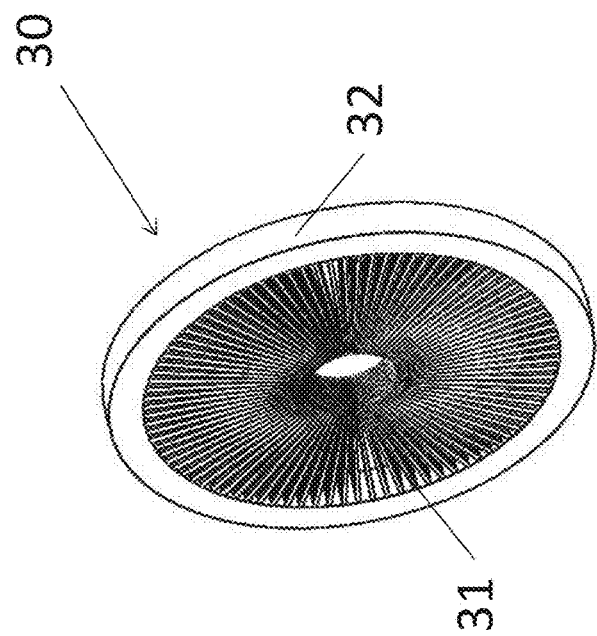

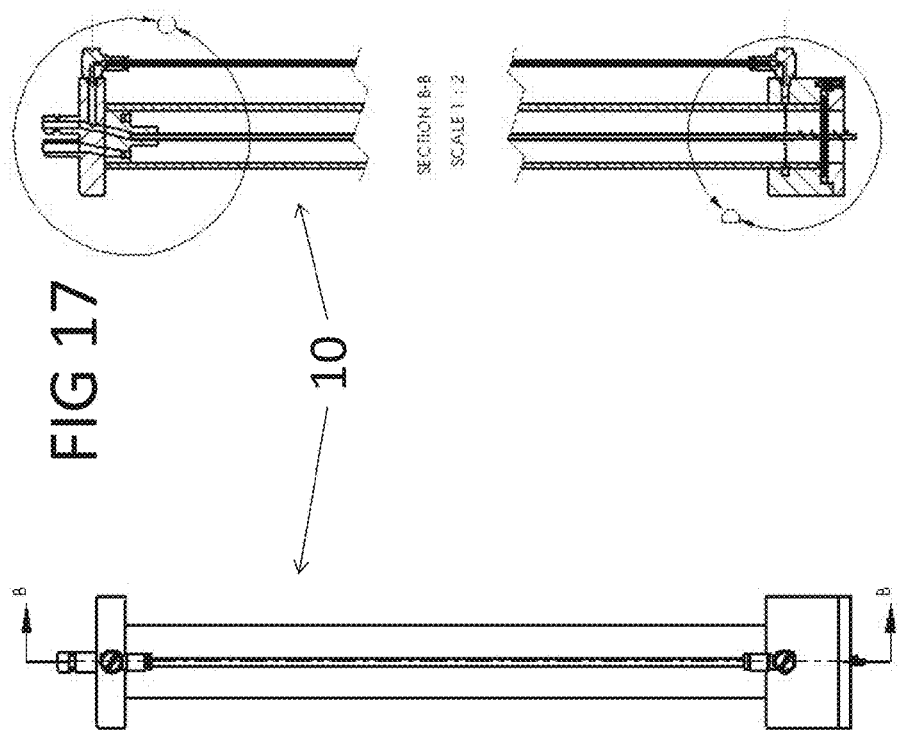

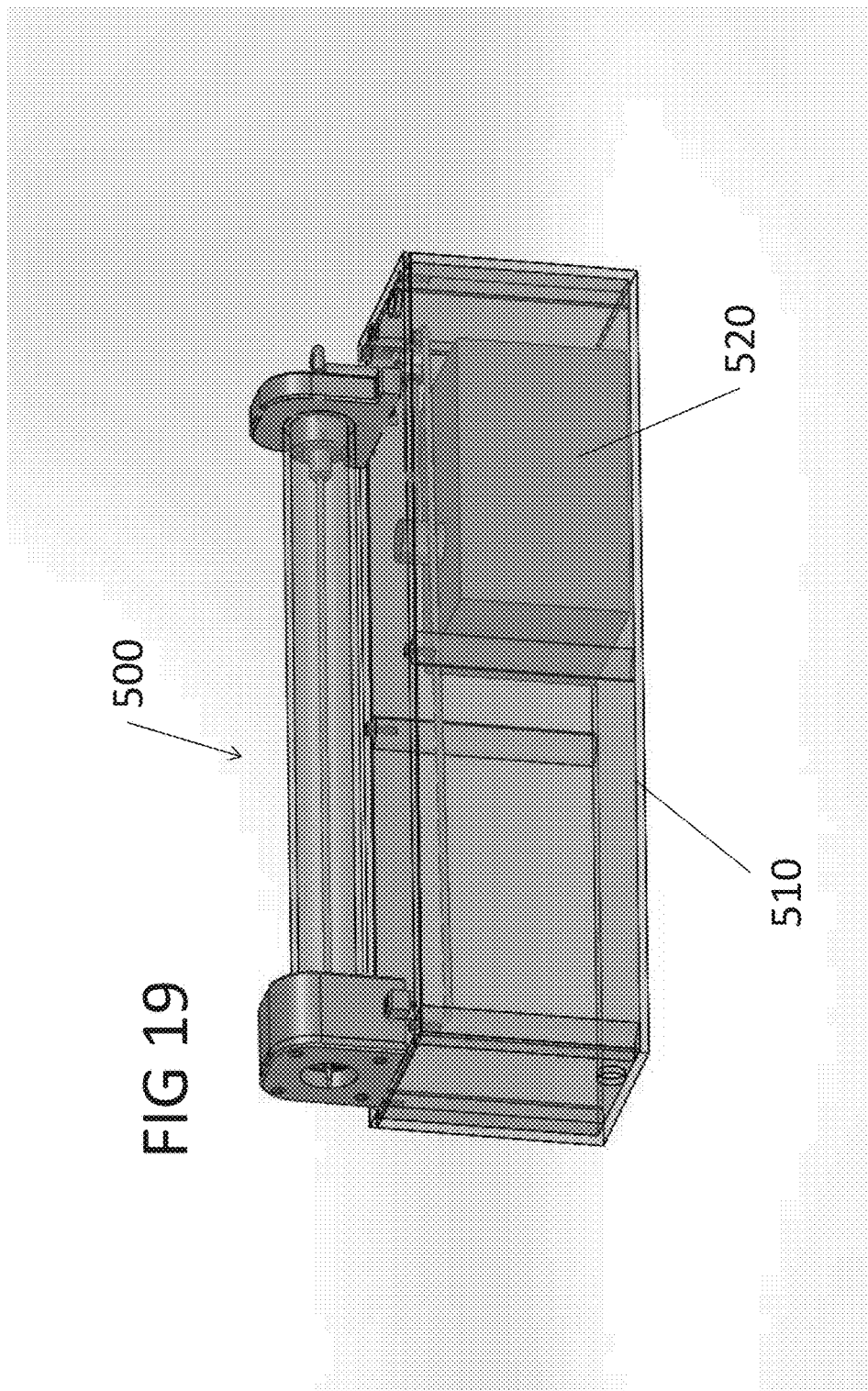

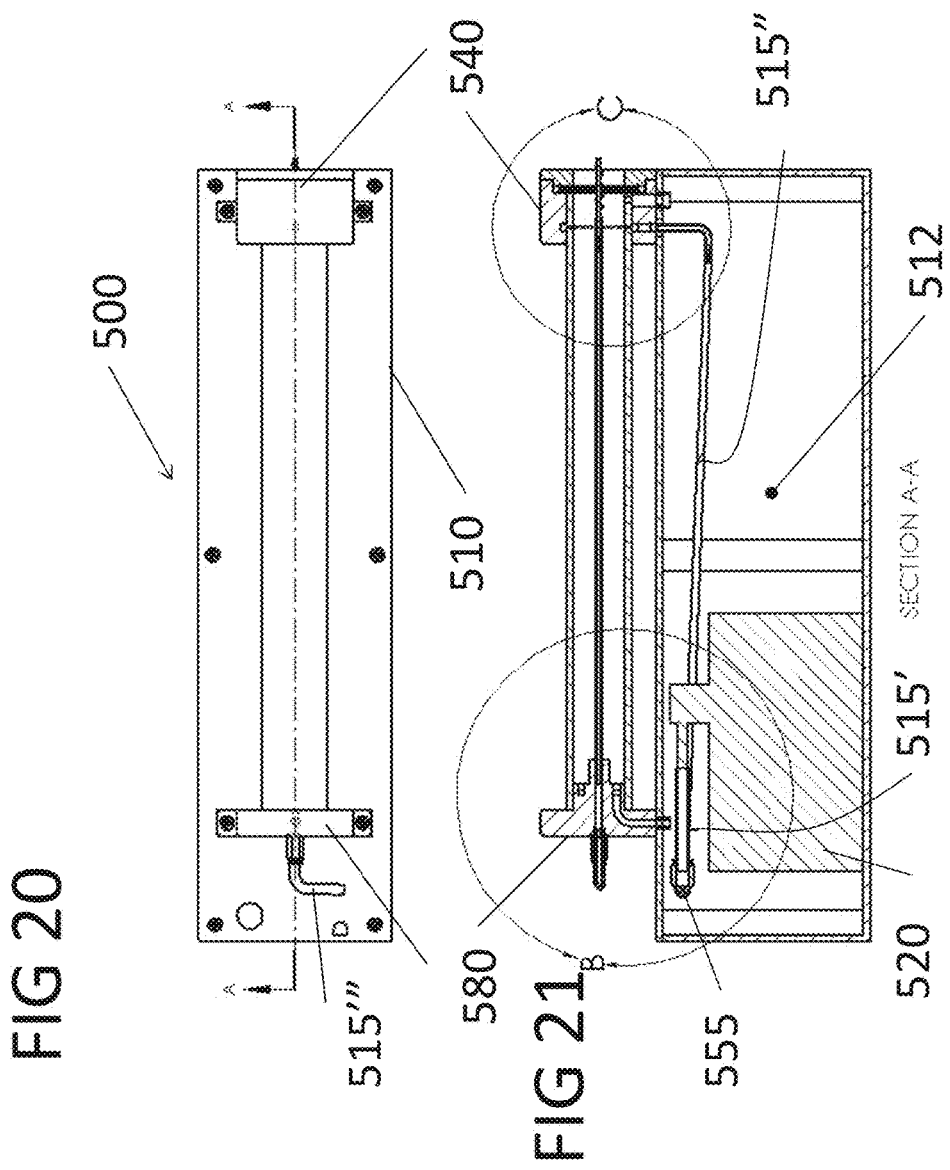

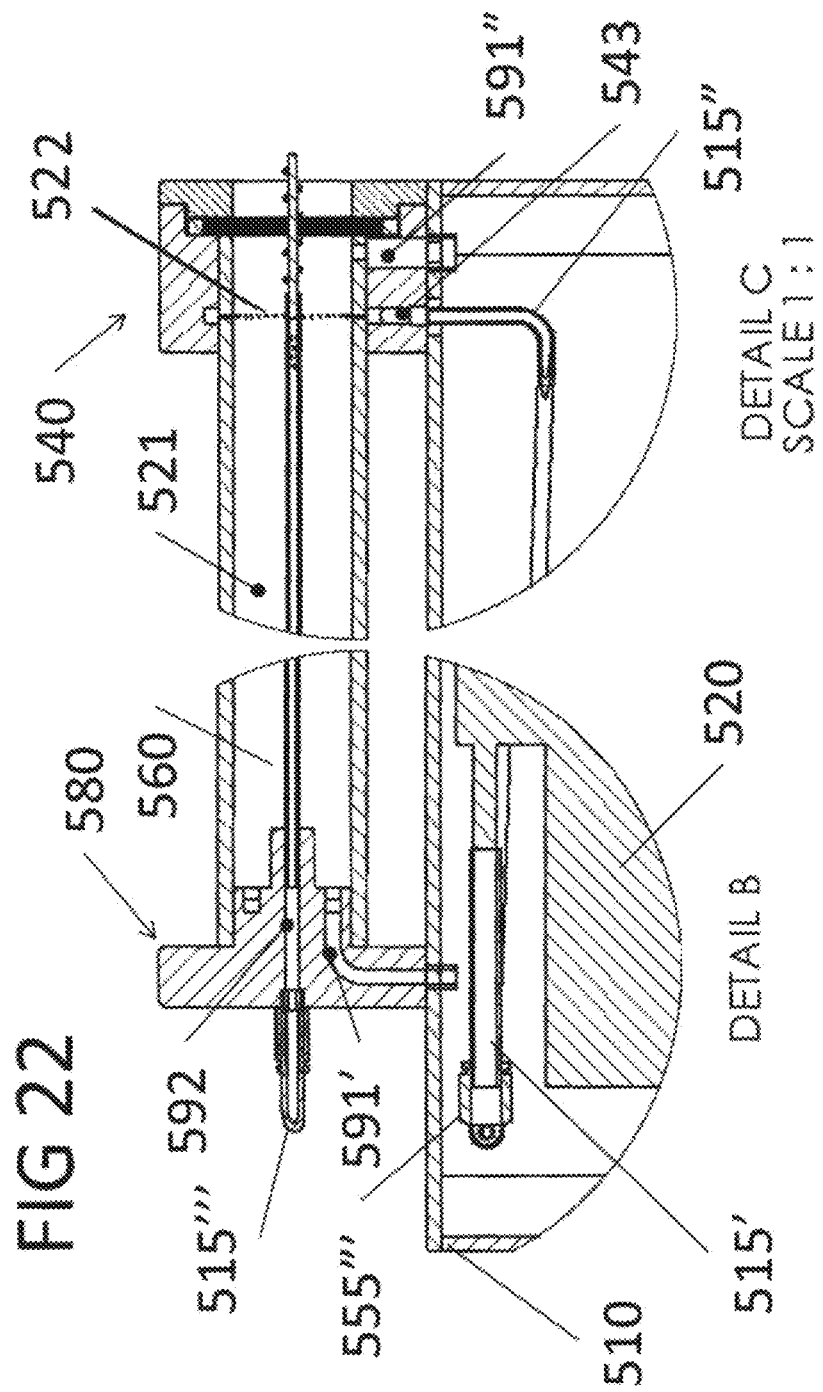

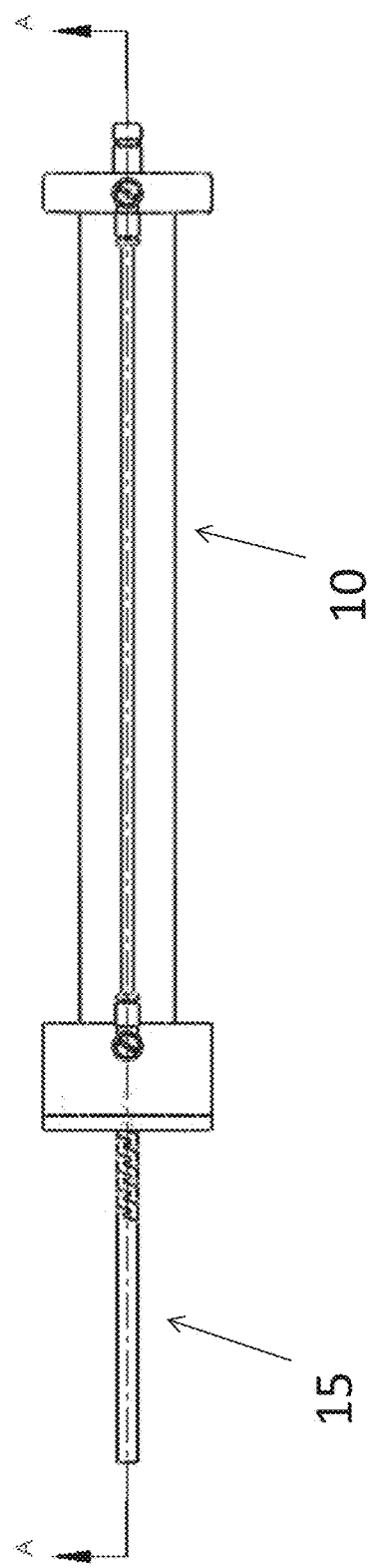

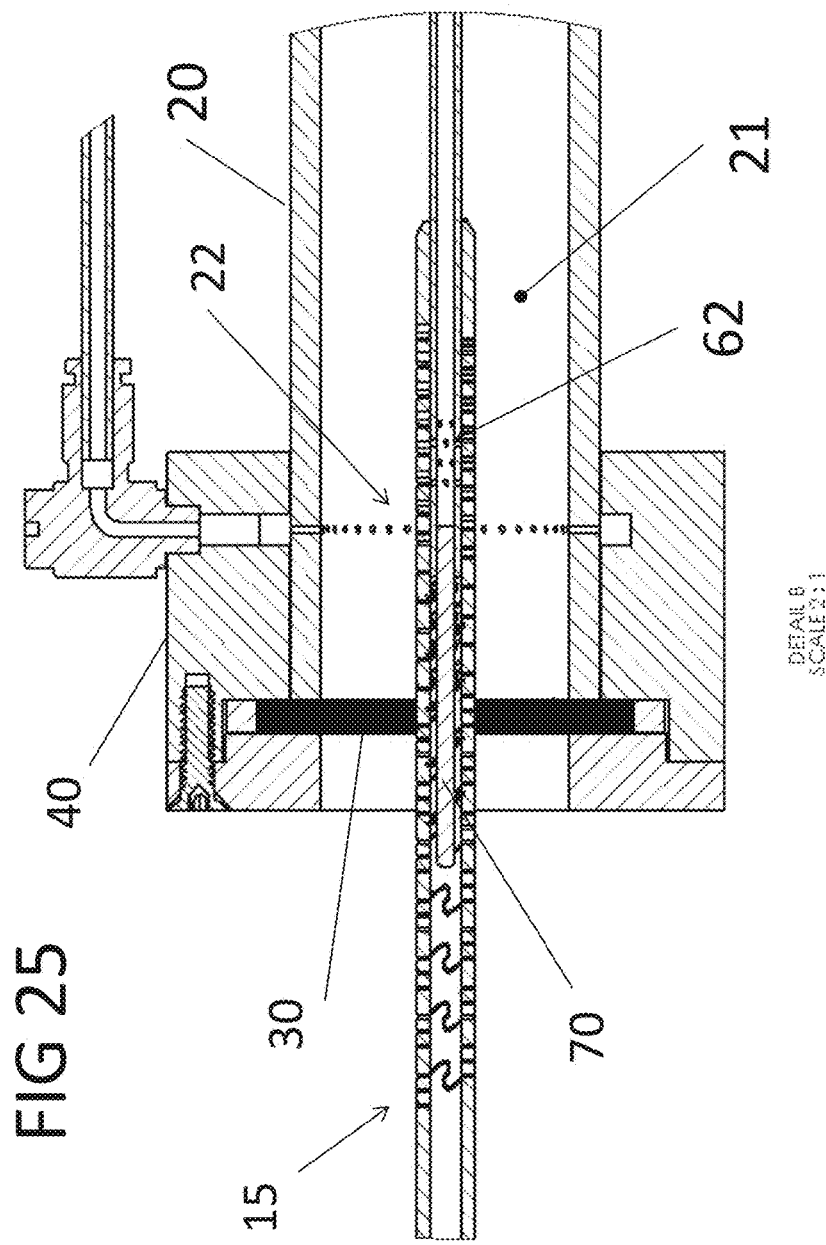

CANNULATED INSTRUMENT FLUSHING AND CLEANING INSTRUMENT

FIELD OF THE INVENTION

The present invention is in the field of cleaning and decontaminating surgical instruments and other medical devices used in healthcare facilities.

BACKGROUND OF THE INVENTION

Medical procedures often involve the use of cannulated flexible shafts, endoscopes and other elongated instruments which are inserted through surgical openings. These medical instruments are relatively expensive products and must be used multiple times. Accordingly, such devices of necessity must be cleaned and sterilized repeatedly. Such instruments typically include long narrow cannulas through which surgical implements and other devices are passed in a surgical procedure. Both the interior and exterior of such cannulas thus are subject to contamination by bodily fluids and materials and must be cleaned carefully before reuse. If they are not thoroughly cleaned prior to disinfection and sterilization, surgical debris can be passed to another patient leading to infection or other complications. Accordingly, it is very important to adequately clean the interiors of endoscopes and similar surgical instruments, which are often difficult to access.

Various techniques or devices have been previously proposed for cleaning the cannulas of the medical devices, the simplest of which involves immersing the devices in solutions containing a detergent and/or an enzyme. Other applications use a small brush, constructed much like the conventional bottle brush having bristles locked between twisted wires, to reach the interior lumen of the cannula. Such brushes are not entirely effective as they do not carry the cleaning or enzymatic solution to the wall surfaces of the lumen. In addition, the bristles are liable to scratch or damage the interior surfaces of the endoscopes and leave hardened deposits thereon.

One solution to this problem was proposed in the United States Patent Application Publication No. US 2003/0213501A1 in which a hydrophilic polyurethane coating is deposited on the bristles of a conventional endoscopic cleaning brush. This coating is used to absorb an enzymatic cleaner and bring the cleaner to the interior surface of the lumen.

Another solution to this problem was proposed by U.S. Pat. No. 5,488,761 in which a tube is configured and dimensioned to slide within the cannula. Pressurized water or a cleaning solution is forced through apertures to clean the inside of the slots. However, U.S. Pat. No. 5,488,761 doesn't address the problem of the pressurized water spraying out through holes, slots and other openings in the device or of the collection of the fluid.

Neither of these solutions address the outer surface of the device which may also have debris adhered to the surface. The art of cleaning the outer and inner surfaces of pipes is well known in the plumbing industry as hardware and home improvement stores sell cleaning tools (i.e. Worthington fitting brush, Item #35172, www.Lowes.com, Oatey 4-in-1 fitting brush, Model #313482, www.homedepot.com) for cleaning cooper and plastic pipes prior to soldering or gluing, respectively. United States Patent Applications US 20040255414A1, 20040031112A1 and 20110005012A1 describe representative devices although those sold in retail stores are much simpler.

SUMMARY OF THE INVENTION

Accordingly, it is a primary object of the present invention to provide an instrument cleaning apparatus capable of flushing gross debris from a cannulated instrument.

It is another object of the present invention to provide an instrument cleaning apparatus that is capable of flushing gross debris from a cannulated instrument, containing the flushing fluid and providing drainage of the flushing fluid.

It is another object of the present invention to provide an orthopedic cannulated instrument cleaning apparatus that is simple, convenient and easy to use.

It is another object of the present invention to provide an orthopedic cannulated instrument cleaning apparatus that is inexpensive and easy to manufacture.

An apparatus for cleaning cannulated surgical tools comprises a hollow body with lavage fluid holes at a first end along with a brush adaptor that is permanently or removably affixed to the hollow body. The brush adaptor has a central cavity to receive the first end of the hollow body, a lavage fluid chamber to receive the lavage fluid holes, and a disk cavity. A disk brush having bristles dimensioned to fit within the disk cavity is maintained within the cavity by an adaptor cover. The disk brush and adaptor cover can be permanently or removably affixed to the brush adaptor.

An inlet adaptor, having a first and second surface, is affixed, permanently or removably, to a second end of the hollow body. A body hub, dimensioned to receive the hollow body, extends from the first surface of the adaptor. The body hub consists of a lavage tube hub dimensioned to receive an inner lavage fluid tube and is in liquid communication with the inner lavage fluid tube through a lavage fluid orifice. The body hub has lavage fluid openings in fluid communication with the hollow body to enable lavage fluid drainage. A lavage fluid hub extends from the second surface of the body hub and is in liquid communication with tube hub through a lavage inlet channel. A lavage fluid hub, containing a lavage fluid channel, is in liquid communication with the hollow body and a lavage fluid chamber. A lavage inlet channel is in liquid communication with the lavage fluid tube hub as well as an upper connecting lavage fluid orifice. The upper connecting lavage fluid orifice permits liquid communication between the lavage fluid connection tube and the lavage fluid inlet channel and radial lavage fluid inlet channel. A suction member can be connected to the lavage fluid channel to remove the lavage fluid.

A lavage connection tube is in liquid communication with hollow body at the brush adaptor and through the upper connecting lavage fluid orifice. The lavage fluid connection tube is in liquid communication with the brush adaptor and upper connecting lavage fluid orifice through connectors permitting fluid passage.

An inner lavage fluid tube, having an inner channel, extends within the hollow body with a distal end in liquid communication through the inner channel and at a proximal end of the inner channel within the inlet adaptor. There are multiple spray openings proximate the distal end of the inner lavage fluid connection tube and a tube brush is dimensioned to fit within the inner channel. The tube brush can be removable or permanently affixed to the inner lavage fluid connection tube.

The apparatus can be provided with attachment members and combined with a reservoir. The reservoir has a top with multiple tube receiving areas, an opposing bottom, sides and ends. A pump within the reservoir has a power source and a number of connection tubes to enable fluid to flow between the apparatus and the reservoir. A first tube connects the reservoir to the inlet channel and a second connects the reservoir to the lavage fluid channel. The pump pumps lavage fluid through the first connection tube and a second connection tube drains lavage fluids from the hollow body.

The cleaning of the cannulated tools uses an apparatus having a hollow body with lavage fluid holes at a first end, with a brush adaptor affixed to the first end and an inlet adaptor affixed to the second end. An exterior lavage fluid tube has a first end in liquid communication with the hollow body through the brush adaptor and a second end in liquid communication with the hollow body through an inlet adaptor. The distal end of a lavage fluid tube from a lavage fluid source is attached to a lavage fluid hub on said inlet adaptor. The distal end of a lavage fluid tube is attached to the lavage fluid hub on the inlet adaptor. The proximal end of an inner lavage fluid tube is attached to the lavage fluid hub and a bristled disk brush attached to the brush adaptor. A brush is attached to the distal end of the inner lavage fluid tube.

The cannulated tool to be cleaned is inserted through the disk brush and over the brush. Lavage fluid from the lavage fluid source enters the lavage fluid hub and travels to the inlet channel and into the inner lavage fluid tube. The lavage fluid from the inner lavage fluid tube exits holes at the end of the inner lavage fluid tube, spraying an interior surface of the cannulated tool. Lavage fluid entering the lavage fluid hub also enters the radial lavage fluid inlet channel and flows along the lavage connecting tube. Lavage fluid leaves the lavage fluid connecting tube and enters the brush adaptor, exiting holes within the brush adaptor, spraying lavage fluid on the exterior of the tool. Lavage fluid exits the hollow body through the lavage fluid hub.

BRIEF DESCRIPTION OF THE DRAWINGS

Embodiments of the present disclosure will now be described, by way of example only, with reference to the attached Figures, wherein:

FIG. 6 is the end view of the entry adaptor and section A-A, in accordance with the present invention.

FIG. 7 is the cross section A-A of the entry adaptor, in accordance with the present invention.

FIG. 8 illustrates the inlet adaptor, in accordance with the present invention.

FIG. 10 illustrates the back face of the inlet adaptor and the position of section C-C, in accordance with the present invention.

FIG. 11 is the cross sectional view through the inlet adaptor of section C-C of FIG. 10, in accordance with the present invention.

FIG. 12 is an illustration of the exterior brush, in accordance with the present invention.

FIG. 16 is a top view of the assembly with position of the section cut B-B, in accordance with the present invention.

FIG. 17 is the view of the assembly through section B-B of FIG. 16, in accordance with the present invention.

FIG. 19 illustrates the overall view of the cleaner assembly of another embodiment in which the cleaner assembly is a self-contained unit having a cleaning fluid reservoir and pump in accordance with the present invention.

FIG. 20 shows the top view of the embodiment of FIG. 19 and the location of Section A-A, in accordance with the present invention.

FIG. 21 shows the sectional view A-A in FIG. 20 and the location of detail areas B and C, in accordance with the present invention.

FIG. 22 shows detail views of areas B and C of FIG. 21, in accordance with the present invention.

FIG. 23 shows the initiation of cleaning whereby the instrument 15 is inserted into the cleaning unit 10 and the location of Section A-A, in accordance with the present invention.

FIG. 25 shows the detail view of area B of FIG. 24, in accordance with the present invention.

GLOSSARY

Figure 1:
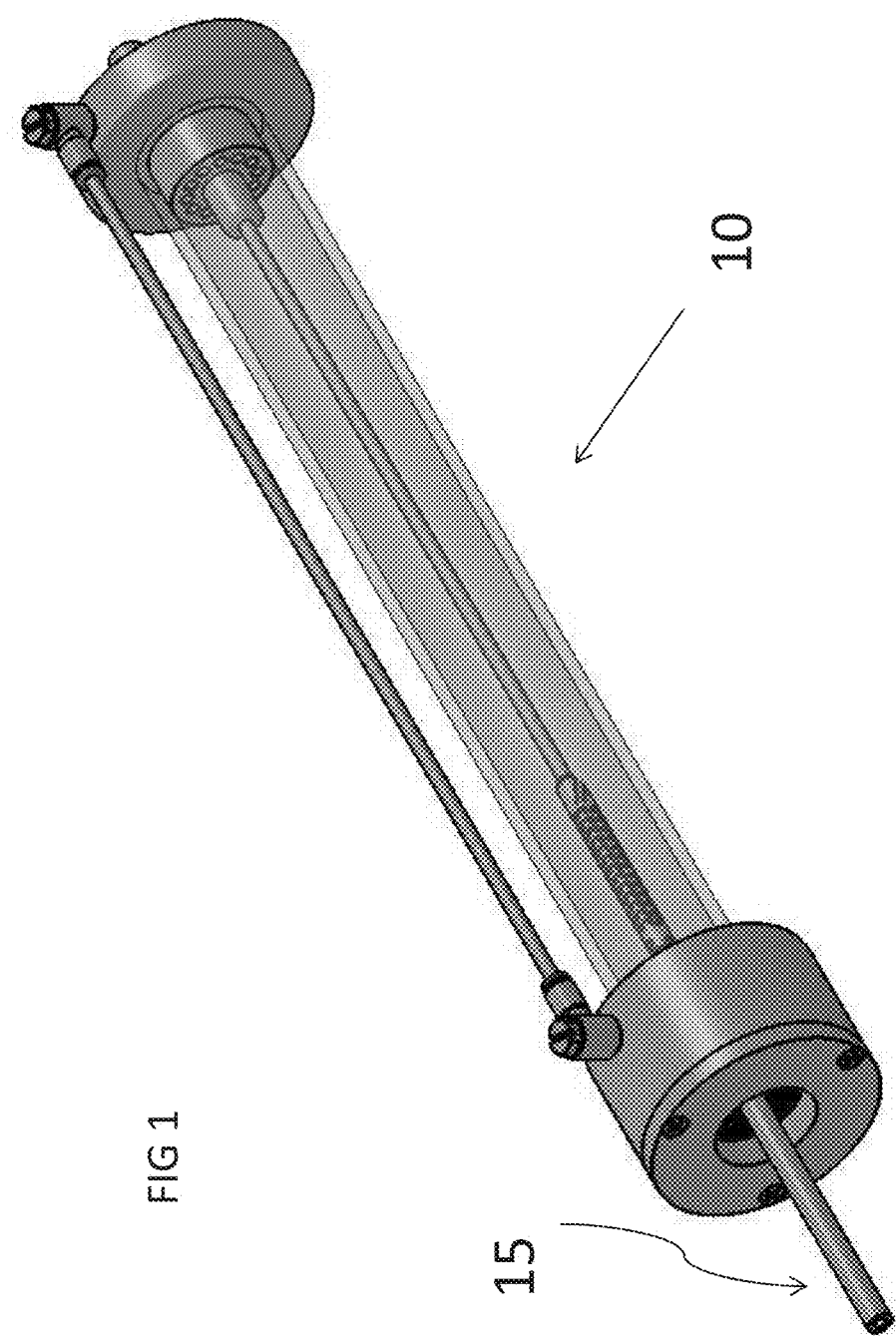
FIG. 1 shows a flexible reamer being inserted in the cleaner assembly, in accordance with the present invention.

For ease of reference, the component numbers used in the Figures are as follows:
10 cleaning device
15 cannulated tool
20 tubular body
21 interior cavity of tubular body
22 lavage fluid holes
30 disk brush
31 inner bristles
32 outer channel
35 brush adaptor cover
37 screws
40 brush adaptor
41. central cavity
42 disk brush cavity
43 lavage fluid chamber
44 lavage fluid chamber inlet
47 screw holes
50 lavage fluid connecting tube
55', 55" connectors
60 inner lavage fluid tube
61 distal end of inner lavage fluid tube 60
62 inner lavage fluid spray openings
63 proximal end of inner lavage fluid tube 60
64 internal channel of the lavage fluid tube.
70 tube brush 80 inlet adaptor
81 interior surface
82 main body
83 body hub
84 lavage fluid tube hub
85 lavage fluid orifice
86 drain openings
87 connecting lavage fluid orifice
88 exterior end
89 drain hub
90 lavage fluid hub
91 drain channel
92 lavage fluid inlet channel
92' radial lavage fluid inlet channel
93 O-ring notch
94 fluid drain chamber
500 self contained cleaning device
510 reservoir
512 reservoir cavity
515", 515"', 515"'' connecting tubing
520 pump
521 tube cavity
540 brush adaptor
543 lavage fluid chamber
555 T-connector
560 inner lavage fluid tube
580 inlet lavage fluid bracket
591', 591" drain channel
592 inlet channel

DESCRIPTION OF THE PREFERRED
EMBODIMENT

Definitions

As used herein the term "tubular" refers to a hollow body having a cross section of one or more sides.

As used herein the term "lavage fluid" refers to the cleansing, or cleaning, fluid used for flushing and/or irrigating a medical tool, device or instrument.

The present invention is specifically related to an apparatus and process for cleaning surgical instruments by flushing the cannulated instrument with a lavage fluid for debris removal. More particularly, the present invention is directed to an apparatus for forcing a lavage, or cleaning, solution through a cannulated surgical instrument, such as a reamer, to remove gross debris from surgery. The apparatus utilizes a fluid lavage fluid system or other source of pressurized lavage fluid solution to provide the motive power required for forcing a lavage fluid through the cannula of a cannulated instrument. In a preferred embodiment, the present invention includes pressurized tanks for delivering a steady flow of flushing solutions through a cannulated instrument.

The cleaning of these instruments has posed a problem since their conception and has been addressed in several methods. One solution was proposed in the US Application Publication No. US 2003/0213501A1 in which a hydrophilic polyurethane coating is deposited on the bristles of a conventional endoscopic cleaning brush. This coating is used to absorb an enzymatic cleaner and bring the cleaner to the interior surface of the lumen. Another solution to this problem was proposed by U.S. Pat. No. 5,488,761 in which a tube is configured and dimensioned to slide within the cannula. Pressurized water or a lavage fluid solution is forced through apertures to clean the inside of the slots. However, U.S. Pat. No. 5,488,761 doesn't address the problem of the pressurized water spraying out through holes, slots and other openings in the device or of the collection of the fluid. Neither of these solutions address the outer surface of the device which may also have debris adhered to the surface.

A first exemplary embodiment of the cleaning device 10 according to the invention is illustrated in FIGS. 1 to 18. The cleaning device 10 is used to clean the interior and exterior surfaces of a cannulated tool 15 as illustrated in FIG. 1. An example of a cannulated tool 15 includes but is not limited to a flexible reamer (shown in FIG. 1).

Figure 2:
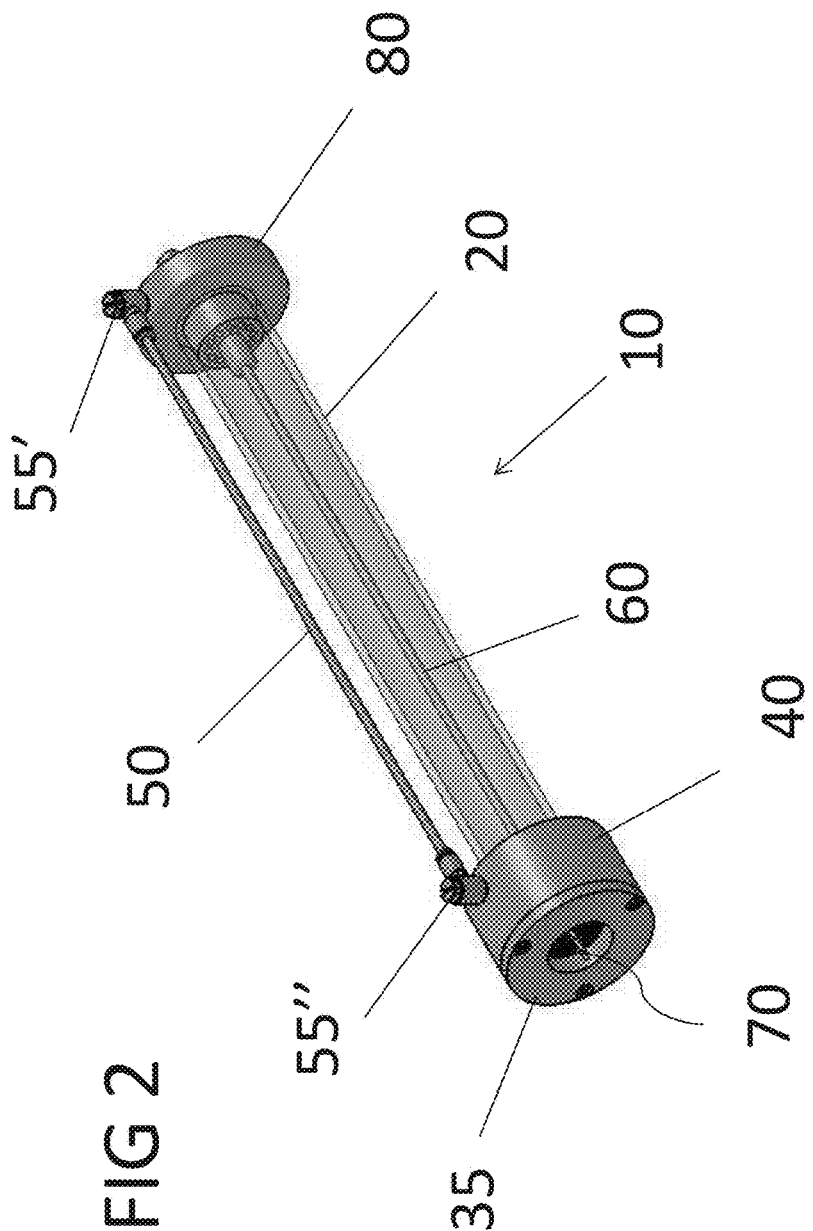
FIG. 2 illustrates the overall view of the cleaner assembly, in accordance with the present invention.

As seen in FIG. 2, the device 10 is generally comprised of a transparent tubular body 20 supported by an inlet adaptor 80 at one end and a brush adaptor 40 at the other end with a brush adaptor cover 35 attached to the brush adaptor 40. A lavage fluid connecting tube 50 spans the length of tubular body 20 and is connected to brush adapter 40 by lavage fluid connector 55" and to inlet adaptor 80 by lavage fluid connector 55'. The inlet adaptor 80 provides lavage fluid connection for the lavage fluid connector 55' and inner lavage fluid tube 60 as well as a drainage connection (not shown). The brush adaptor 40 allows for the protrusion of the inner lavage fluid tube 60 and tube brush 70. Tube brush 70 and inner lavage fluid tube 60 receive and pass through the interior of cannulated tool 15 of FIG. 1. The tubular body 20 surrounds the exterior surface of cannulated tool 15 when the tool is inserted into device 10. Preferably the tubular body 20 is a clear or transparent polymer material to allow observation of insertion of the tool being cleaned.

Figure 3:
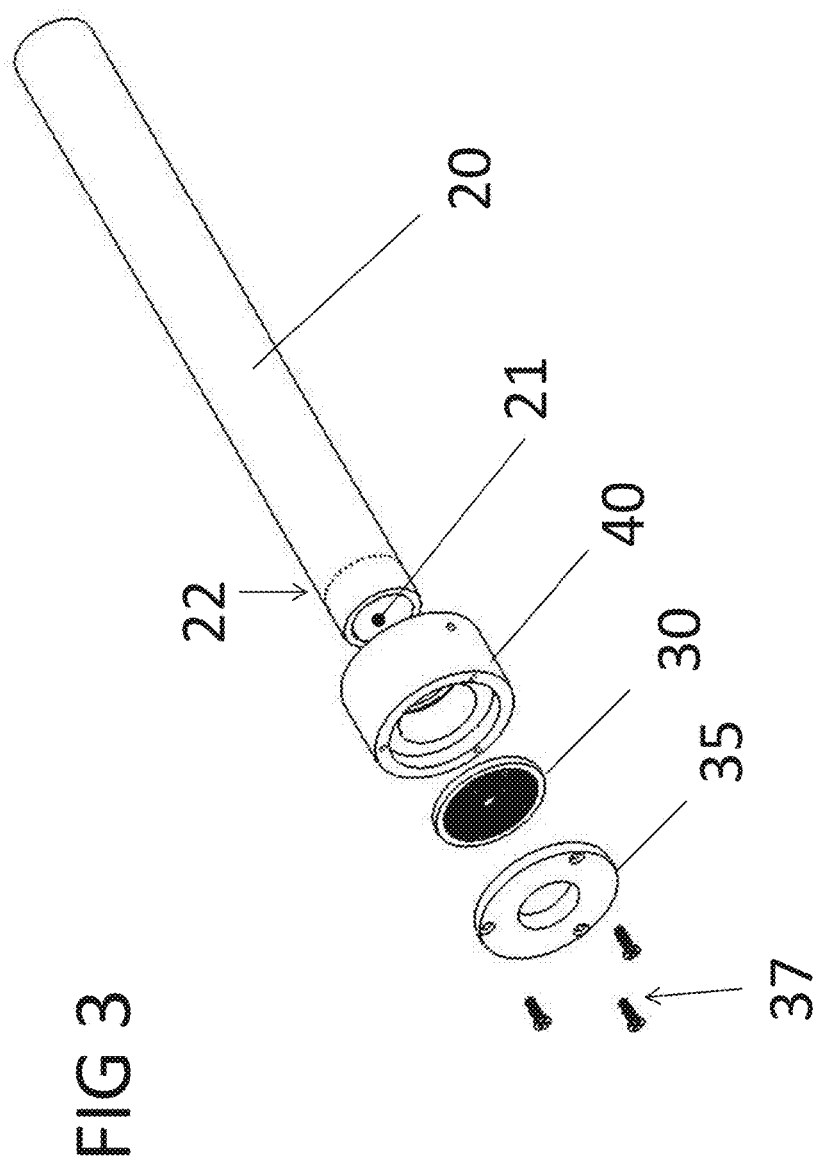
FIG. 3 shows an exploded view of the outer parts of the assembly, in accordance with the present invention.

FIG. 3 shows an exploded drawing of the outer components of the device 10. The tubular body 20 includes multiple lavage fluid holes 22 which allow the lavage fluid to spray on the cannulated tool to be cleaned. The lavage fluid holes 22 are preferably equally spaced around the tubular body 20 and dimensioned to permit liquid flow. Tubular body 20 fits securely within the brush adaptor 40 that houses a disk brush 30. The brush adaptor cover 35 holds the disk brush 30 in the brush adaptor 40 through the use of multiple screws, bolts 37 or other applicable means, either removable or non-removable.

Figure 4:
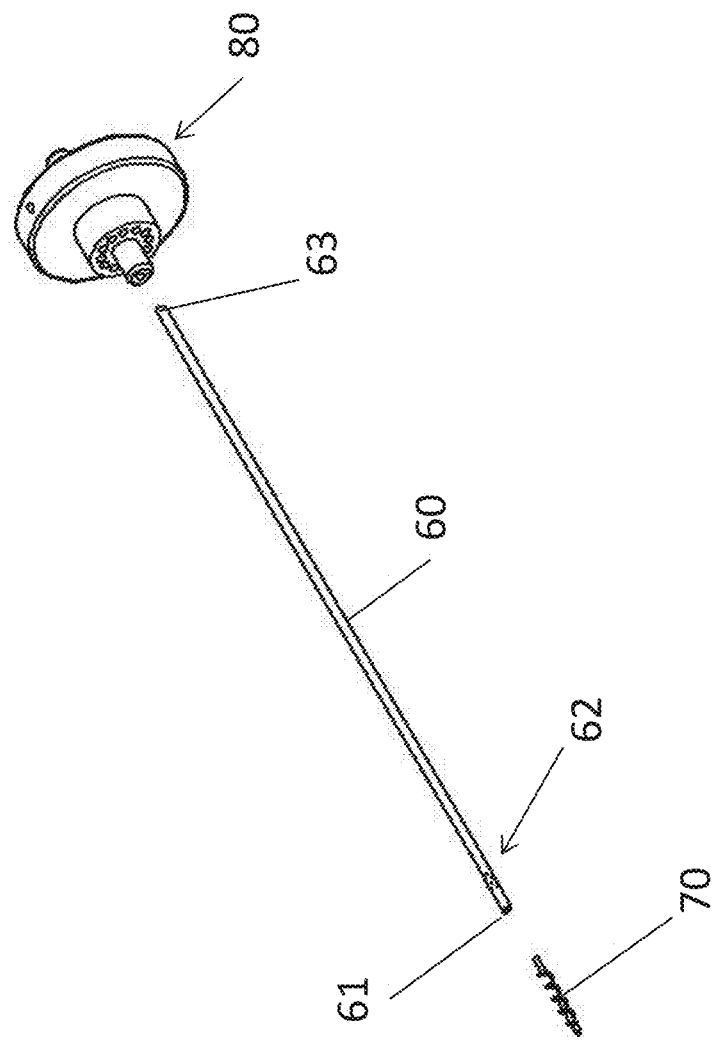
FIG. 4 shows an exploded view of the inner parts of the assembly, in accordance with the present invention

FIG. 4 shows an expanded drawing of the inner lavage fluid components of the device 10. The tube brush 70 is attached to the distal end 61 of the inner lavage fluid tube 60. The tube brush 70 can be attached to the inner lavage fluid tube 60 in either a removable or non removable manner such as threaded, friction fit, press fit and glued, or welded. Removability enables the replacement of the brush 70 which can be advantageous for some, but not all, applications. The inner lavage fluid tube 60 has multiple inner lavage fluid spray openings 62 around the diameter proximate its distal end 61. As these openings 62 are for spraying lavage fluid, they should be placed completely around the tube 60 and have a sufficient size as to permit fluid to be sprayed there through. The proximal end 63 of the inner lavage fluid tube 60 is attached to the inlet adaptor 80. At proximal end 63, lavage fluid tube 60 can be removable or non-removable from the inlet adaptor 80; however, removability permits non cannulated devices to be cleaned. Inlet adaptor 80 can also be removable from device 10 to allow use of different adaptors having different size lavage fluid tubes or no tube at all. The removability of either the lavage fluid tube or the inlet adaptor would be a manufacturing preference and dependent upon end use.

Figure 5:
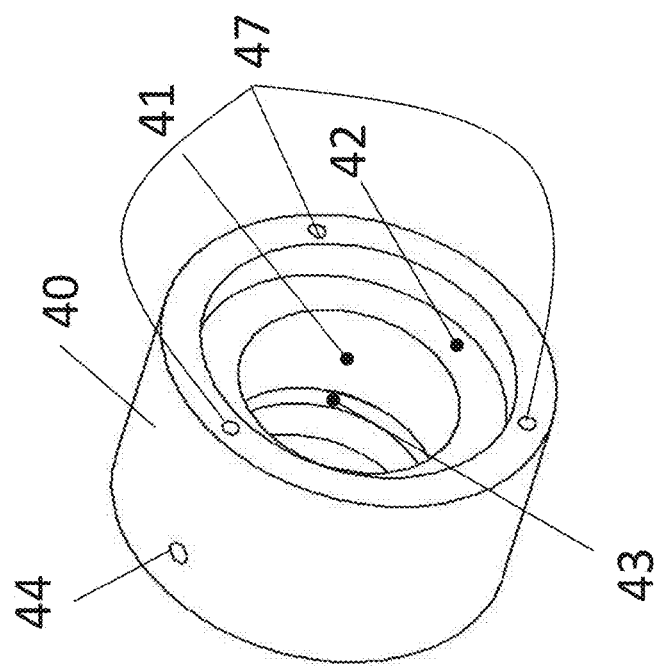
FIG. 5 illustrates the entry lavage fluid and external brush holding adaptor, in accordance with the present invention.

FIG. 5 shows an isometric view of the brush adaptor 40 with a central cavity 41 into which the tubular body 20 is inserted such that the lavage fluid holes 22 of the tubular body 20 (shown in FIG. 3) align with the lavage fluid chamber 43. The central cavity 41 is in liquid communication with the lavage fluid chamber inlet 44. Also shown is the disk brush cavity 42 for placement of the disk brush 30. Screw holes 47 are dimensioned to receive the screws 37 used to attach the brush adaptor cover 35 (shown in FIG. 3). Alternatively a stop can be added, either as tabs or a lip, to place the tubular body 20 in a position to ensure that the lavage fluid holes 22 align with the lavage fluid chamber 43.

FIG. 6 is the end view of the brush adaptor 40 and illustrates the location of section A-A which is shown in detail in FIG. 7. In FIG. 7, the section A-A view shows the central cavity 41 within brush adaptor 40, the location of the disk brush cavity 42 at one end of brush adaptor 40, and the location of lavage fluid chamber 43 near the other end of brush adaptor 40. As can be seen in FIG. 7, lavage fluid chamber 43 is connected to lavage fluid chamber inlet 44. Screw holes 47 are also shown.

FIG. 8 shows an isometric view of the inlet adaptor 80 with a main body 82 having an upper connecting lavage fluid orifice 87 and a first surface 81. Extending from the first surface 81 is a body hub 83. The body hub 83 has drain openings 86 for removing lavage fluid and is dimensioned to fit into the interior diameter of the tubular body 20 which abuts the first surface 81. The fit between the body hub 83 and the interior diameter of the tubular body 20 is such that the tubular body 20 can be removed without damage, but does not rotate or otherwise move on the hub 83. Extending from body hub 83 is a lavage fluid tube hub 84 over which the inner lavage fluid tube 60 is placed for attachment. Again, the fit between the interior diameter of the inner lavage fluid tube 60 and the outer diameter of the lavage fluid tube hub 84 should be such that permits minimal movement while still enabling removal. Lavage fluid tube hub 84 has a lavage fluid orifice 85 which connects to proximal end 63 of inner lavage fluid tube 60.

Figure 9:
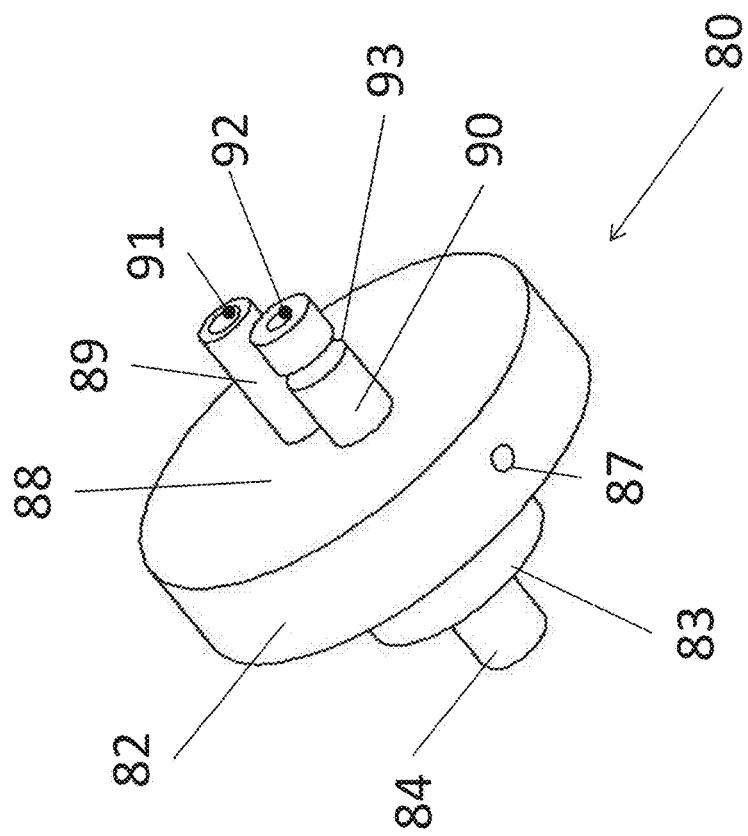
FIG. 9 illustrates the back side of the inlet adaptor, in accordance with the present invention.

FIG. 9 shows another isometric view of the exterior end 88 of the inlet adaptor 80. A lavage fluid source (not shown) connects to lavage fluid hub 90 such that the fluid passes through lavage fluid inlet channel 92 and exits through lavage fluid orifice 85 (FIGS. 8 and 11) within tube hub 84 and into lavage fluid tube 60 which is attached to tube hub 84. An o-ring groove 93 holds an o-ring (not shown) to provide a seal to prevent leakage of fluid. An upper connecting lavage fluid orifice 87 on the main body 82 of the inlet adaptor 80 connects the inlet adaptor 80 to connector 55' of FIG. 2. To remove the lavage fluid from device 10, a suction or drain tube is attached on drain hub 89 having a drain channel 91. Fluid passes through the drain openings 86 of body hub 83 (shown in FIG. 8) into drain channel 91 and out of device 10.

FIG. 10 is an end view of exterior end 88 of the inlet adaptor 80 showing locations of the lavage fluid hub 90 and drain hub 89. The location of Section C-C is shown in FIG. 11 where the interior of the lavage fluid inlet adaptor 80 is illustrated. The lavage fluid inlet channel 92 extends through lavage fluid hub 90 into the main body 82 and through the body hub 83 and lavage fluid tube hub 84. The proximal end 63 of the inner lavage fluid tube 60 is press fitted into the lavage fluid orifice 85 to enable the lavage fluid to flow to the distal end and exit the inner lavage fluid spray openings 62 to clean the interior of the cannulated tool 15. In addition, a lavage fluid inlet channel 92' extends in a radial direction within the main body 82 from the lavage fluid inlet channel 92 to the upper connecting lavage fluid orifice 87 for attachment of the connector 55' to supply fluid to the brush adaptor 40. Similarly, drain channel 91 extends through the lavage fluid inlet adaptor 80 connecting to the concentric fluid drain chamber 94 and drain openings 86 of body hub 83 to drain the lavage fluid by means of a suction or gravity.

FIG. 12 shows an interior disk brush 30 with an outer channel 32 and inner bristles 31 for cleaning the exterior of the cannulated tool 15. The disk brush 30 is restrained within the disk brush cavity 42 of the brush adaptor 40 and the brush adaptor cover 35. The interior disk brushes are commercially available from brush manufactures such as Precision Brush, Solon, Ohio and Carolina Brush, Gastonia, N.C.

Figure 13:
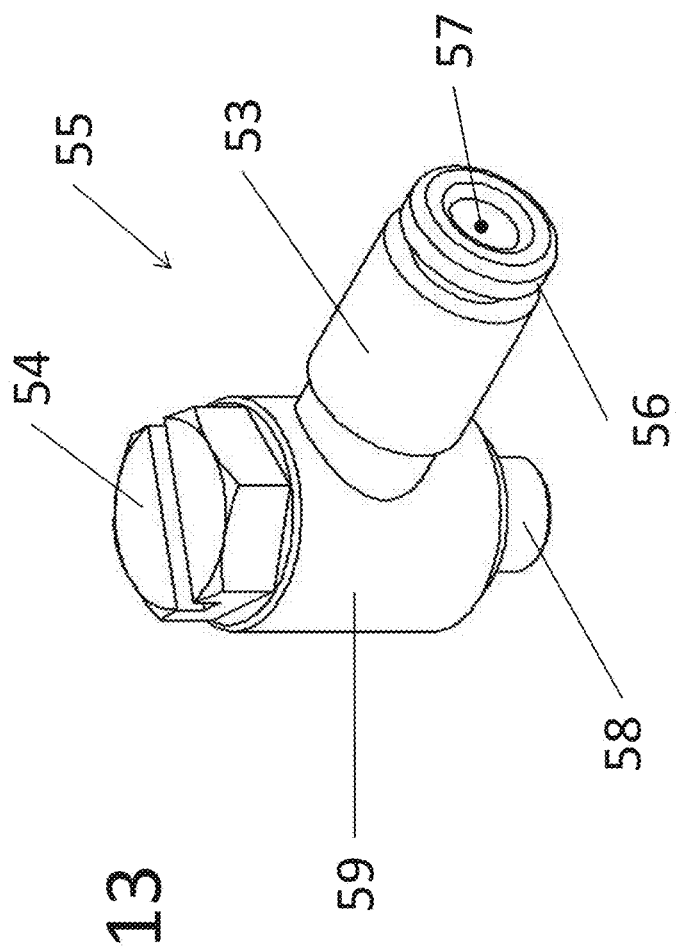
FIG. 13 is an illustration of the tubing connector, in accordance with the present invention.

Each of the connectors 55 (55' and 55" of FIG. 2) as shown in FIG. 13 is a commercially available, quick connect connector for attachment to the brush adaptor 40 and inlet adaptor 80 for connecting the lavage connecting tube 50. The connectors 55, 55' and 55" have an attachment end 58 that is rigidly fixed to the lavage fluid chamber inlet 44 to connect the lavage fluid orifice 87. The connectors 55, 55' and 55" can, using the fixation bolt 54 that passes through the main body 59, be threadably connected at the attachment end 58. The side arm 53 has a quick connect coupling 56, with a channel 57, to receive a lavage fluid connecting tube 50. Although commercially available connectors are preferable, due to cost and availability, other types of connectors suitable to the application can be used.

Figure 15:
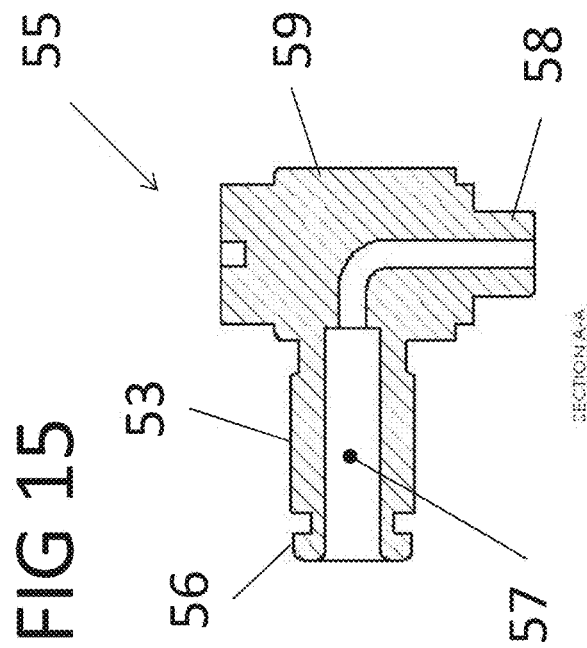
FIG. 15 is the cross section view through section A-A of FIG. 14, in accordance with the present invention.
Figure 14:
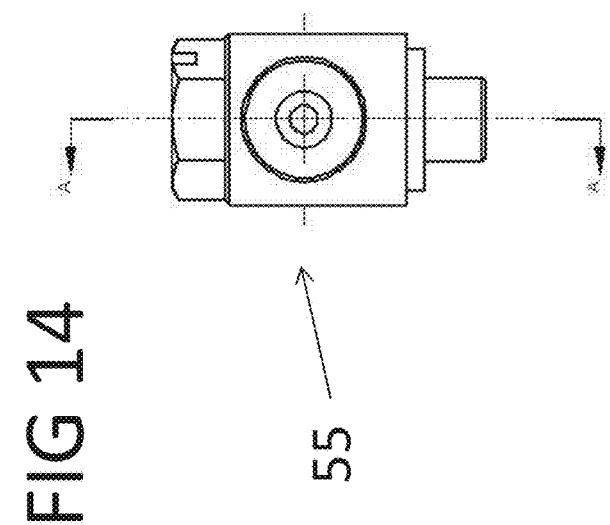
FIG. 14 is a front views of the tubing connector and the position of Section A-A, in accordance with the present invention.

FIG. 14 is a side view of one of the connectors 55 showing the position of Section A-A to illustrate the channel 57 through which lavage fluid flows. FIG. 15 is a cutaway side view of the connector 55 illustrating how the channel 58 runs through the side arm 53 exiting the attachment end 58.

Figure 18:
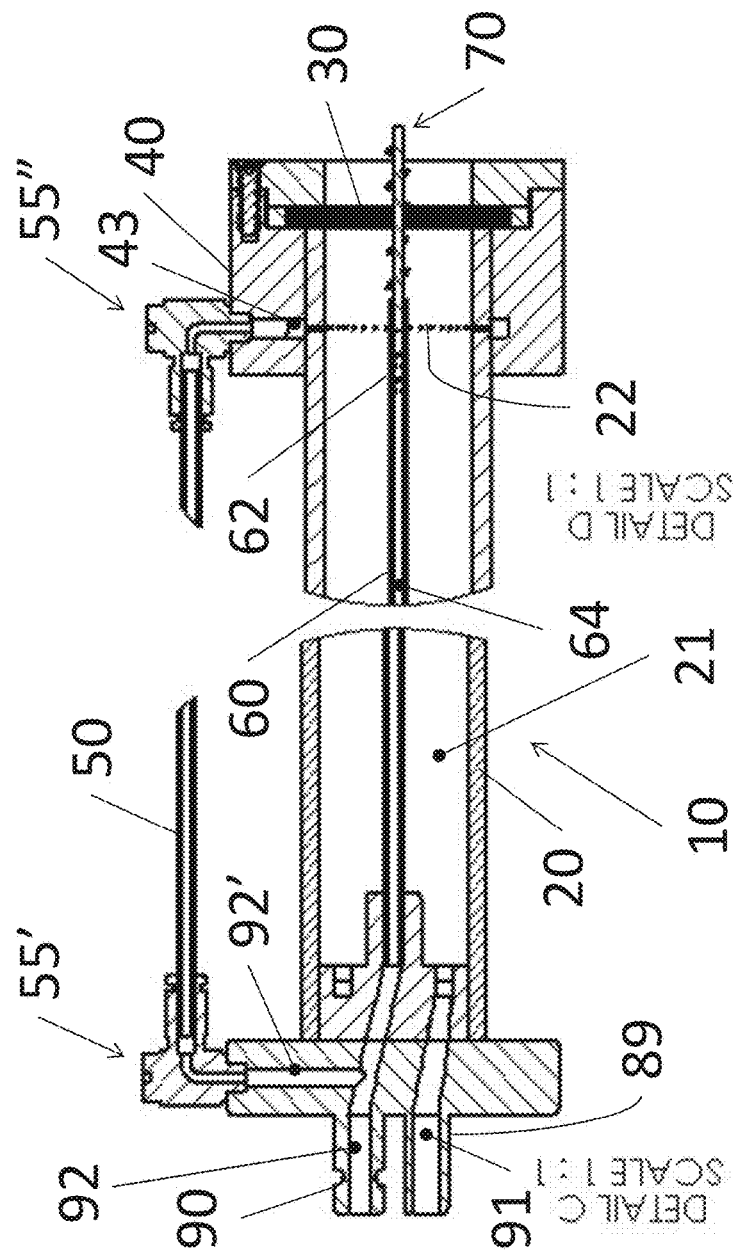
FIG. 18 is detail views of areas C and D shown in FIG. 17 showing flow of lavage fluid through the assembly, in accordance with the present invention.

Lavage fluid is flushed through device 10 to clean cannulated tool 15. FIG. 18 illustrates the interior channels through which lavage fluid is distributed to clean the exterior and interior of the tool 15. FIG. 16 shows the location of Section B-B through the complete unit 10 which is shown in FIG. 17 for the location of detail areas C and D illustrated in FIG. 18. The lavage fluid, from an external source attached to the lavage fluid hub 90, enters the lavage fluid inlet channel 92 and flows into the interior channel 64 of the inner lavage fluid tube 60 to exit from orifices 62 into tubular body 20. In addition, the fluid will flow through the radial lavage fluid channel 92', through the connector 55', connector tube 50, connector 55" and into the lavage fluid chamber 43 then through the lavage fluid holes 22 into tubular body 20. The fluid is drained from the interior cavity 21 of the tubular body 20 through the drain channel 91 in the drain hub 89.

Lavage fluid is thus moved through the interior of the instrument 15 though the interior channel 64 and exits through openings 62 into the inner cavity 21. In addition, fluid is moved through the exterior tube 50 and exits through holes 22 of the tubular body 20 exiting into the inner cavity 21. The drain channel 91, connected to an external suction, is on the opposing end of the device 10 from its entry point, thereby creating a negative pressure within the inner cavity 21 to remove the fluid.

In a second exemplary embodiment of the invention, the cleaning unit shown in FIG. 19-25 is a self-contained unit 500 having a reservoir 510, containing a reservoir cavity 512 containing the lavage fluid and pump 520. Connecting tubing 515' (FIG. 21) provides the lavage fluid to the cleaning apparatus having the basic design detailed in the first embodiment 10 and modified to be affixed to and be in fluid communication with the reservoir 510. In the illustrated embodiment, the water recirculates within the reservoir. The water exiting through the drain channel 591 can also be directed out of the reservoir. Alternatively separate chambers, one with a suction member and one with a pump could also be incorporated, depending on how frequently the cleaning unit would be used.

FIG. 20 illustrates the top view of the cleaning unit 500 and the location of the Section A-A shown in FIG. 21. FIG. 22 illustrates in more detail the connection areas within the cleaning unit 500. Within the reservoir 510 is a pump 520 with outflow tubing 515' connected to a T-connector 555 to direct the fluid to connecting tubing 515" and 515'". Tubing 515' connects to the lavage fluid chamber 543, within the brush adaptor 540 enabling lavage fluid holes 522 to spray lavage fluid over the outer surface of the tool. Tubing 515" connects to the inlet channel 592 to provide fluid to the lavage fluid tube 560. Fluid drains from the tubular body interior 521 through the drain channel 591' in the inlet bracket 580 and drain channel 591" in the brush adaptor 540 into the reservoir cavity 512.

A DETAILED DESCRIPTION OF THE USAGE OF THE INVENTION

Figure 24:
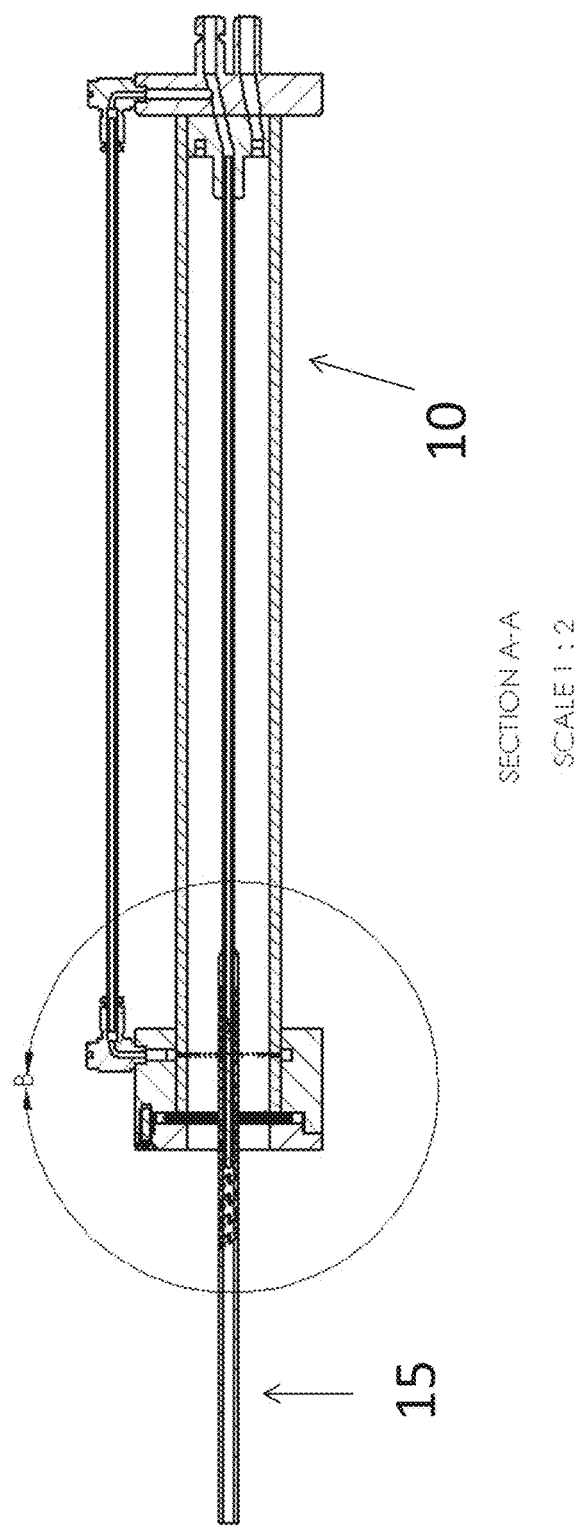
FIG. 24 shows sectional view A-A of FIG. 23 and the location of detail view area B of the instrument 15 inserted into the cleaning unit, in accordance with the present invention.

As shown in FIGS. 1 and 23, a cannulated tool 15, such as a flexible reamer, is to be cleaned using the device 10. The cannulated tool 15, has a helical slot through the wall of the shaft to impart flexibility but the slot also collects tissue and blood which needs to be cleaned after use. The cannulated tool 15 is positioned in FIG. 1 to slide over the tube brush 70 on the end of the inner lavage fluid tube 60 as shown in FIG. 25. The details of FIG. 25 are from detail area B of Section A-A of FIG. 24, the location of which is shown in the top view of cannulated tool 15 of FIG. 23. To use the cleaning device 10 of the present invention to clean a cannulated tool, a lavage fluid source is connected to the lavage fluid hub 90 of the inlet adaptor 80, and a drain tube is connected to the drain hub 89 of the inlet adaptor. The lavage fluid flows through the lavage fluid inlet channel 92 with fluid going straight through the inlet adaptor 80 into the inner lavage fluid tube 60 and out the inner lavage fluid spray openings 62. The tube brush 70 at the end of the inner lavage fluid tube 60 is inserted in the interior of the cannulated tool 15 to physically dislodge any debris in the cannulated tool. The fluid being flushed through the openings 62 is being directly sprayed onto the interior surface of the cannulated tool 15 as the tool is being pushed through the brush adaptor of the device 10 thereby directly and thoroughly cleaning the interior of the tool. The lavage fluid also flows through the radial lavage fluid inlet channel 92", through the connector 55', the lavage fluid connecting tube 50, the connector 55", into the lavage fluid chamber 43 in the brush adaptor 40 and exits through the lavage fluid holes 22 to spray onto the outer surface of the cannulated tool being cleaned as shown in FIG. 24. The outer disk brush 30 dislodges any debris on the outer surface of the cannulated tool. The tube brush 70 and disk bush 30 provide an initial cleaning prior to the lavage fluid. After the lavage fluid has made contact with and cleansed the cannulated tool, the fluid flows into the interior of the tubular body where it passes through the drain openings 86 and is suctioned through the drain channel 91 and out of the device 10. Although the lavage fluid could be left to drain through gravity, the use of a suction member creates a current within the hollow body 20 to more thoroughly and cleanly remove any debris.

FIG. 25 gives a detailed view of the instrument 15 inserted over the tube brush 70 and lavage fluid tube 60 and the circular brush 30 scraping the outer surface of the instrument and the position of the lavage fluid holes 62 in the lavage fluid tube and the inner lavage fluid spray openings 22 in the tubular body 20. The circular brush 30 also acts to minimize the lavage fluid from exiting out the tubular body 20 so it can drain using the ports provided.

BROAD SCOPE OF THE INVENTION

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims (e.g., including that to be later added) are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." In this disclosure and during the prosecution of this application, means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited. In this disclosure and during the prosecution of this application, the terminology "present invention" or "invention" may be used as a reference to one or more aspect within the present disclosure. The language of the present invention or inventions should not be improperly interpreted as an identification of criticality, should not be improperly interpreted as applying across all aspects or embodiments (i.e., It should be understood that the present invention has a number of aspects and embodiments), and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features. In this disclosure, the following abbreviated terminology may be employed: "e.g." which means "for example."

While in the foregoing we have disclosed embodiments of the invention in considerable detail, it will understood by those skilled in the art that many of these details may be varied without departing from the spirit and scope of the invention.

What is claimed is:

1. An apparatus (10) for cleaning cannulated surgical tools (15) comprising:
   a. a hollow body (20) having a first end, said first end having lavage fluid holes (22) and a second end;
   b. a brush adaptor (40, 540), said brush adaptor (40, 540) being removably affixable to said first end of said hollow body (20);
   c. an inlet adaptor (80), said inlet adaptor (80) being removably affixable to said second end of said hollow body (20);
   d, a lavage fluid connecting tube (50), said lavage fluid connecting tube (50) having a first end in liquid communication with said first end of said hollow body (20)

at said adaptor (40) and a second end in liquid communication with said hollow body (20) at said inlet adaptor (80);

e. an inner lavage fluid tube (60, 560), having an inner channel (64), said inner lavage fluid tube (60, 560) extending within said hollow body (20) and having a distal end (61) in liquid communication through said inner channel (64) with said hollow body (20) and a proximal end (63) in liquid communication through said inner channel (64) with said inlet adaptor (80);

f. a reservoir (510); said reservoir (510) having a top and opposing bottom, a pair of opposing sides and a pair of opposing ends, and sealed to contain a lavage fluid, a pump (520) having a power source, said pump (520) being in fluid communication with multiple connection tubes (515',515", 515'''), and said multiple connection tubes (515',515", 515'''), being in fluid communication with multiple tube receiving holes; wherein said pump (520) pumps lavage fluid from said reservoir (510) through said multiple connection tubes.

2. The apparatus of claim 1 wherein said adapter (40) further comprises:
   a. central cavity (41) to receive said first end of said hollow body (20);
   b. a lavage fluid chamber (43) to receive said lavage fluid holes (22);
   c. a disk cavity (42);
   d. a disk brush (30) having bristles (31) dimensioned to fit within said disk cavity (42);
   e. an adaptor cover (35), said adaptor cover (35), maintaining said disk brush (30) within said disk cavity (42);
   f. a lavage fluid chamber inlet (44), said lavage fluid chamber inlet (44), being in liquid communication with said lavage fluid chamber (43) and said lavage fluid connecting tube (50).

3. The apparatus of claim 1 wherein said inlet adaptor (80) has a body (82) with a first surface (81) and a second surface, said inlet adaptor (80) further comprising:
   i. a body hub (83), said hub (83) extending from said first surface (81) and being dimensioned to receive said hollow body (20), said body hub (83) comprising:
      1. a lavage fluid tube hub (84), said lavage fluid tube hub (84) extending from said body hub (83) dimensioned to receive said inner lavage fluid tube (60, 560) and being within liquid communication with said inner lavage fluid tube (60, 560) through a lavage fluid orifice (85);
      2. lavage fluid openings (86) in fluid communication with said hollow body (20) to enable lavage fluid drainage;
   ii. a lavage fluid hub (90), said lavage fluid hub (90) extending from said second surface and comprising:
      1. a lavage fluid hub (89), said lavage fluid hub (89) containing a lavage fluid channel (91) in liquid communication with said hollow body (20) and a lavage fluid chamber (94);
      2. a lavage fluid inlet channel (92) in liquid communication with said lavage fluid tube hub (84);
      3. an upper connecting lavage fluid orifice (87), said upper connecting lavage fluid orifice (87) permitting liquid communication between said lavage fluid connecting tube (50) and said lavage fluid inlet channel (92) and a radial lavage fluid inlet channel (92').

4. The apparatus of claim 1 wherein said inner lavage fluid tube (60, 560) further comprises a tube brush (70) at said distal end (61).

5. The apparatus of claim 1 wherein said inner lavage fluid tube (60, 560) further comprises spray openings (62) around a diameter of said distal end (61).

6. The apparatus of claim 1 wherein said lavage fluid connecting tube (50) further comprises connectors (55) connecting said lavage fluid connecting tube (50) in liquid communication with said inlet adaptor 80 and said adaptor (40, 540).

7. The apparatus of claim 4 wherein said tube brush (70) is removable.

8. The apparatus of claim 1 wherein said at least one of said inlet adaptor (80), said lavage fluid connecting tube (50), said inner lavage fluid tube (60, 560), and said brush adaptor (40, 540) are removable from said hollow body (20).

9. The apparatus of claim 2 wherein said disk brush (30) is removable from said disk cavity (42) by removal of said adaptor cover (35).

10. The apparatus of claim 4 wherein said tube brush (70) is removable from said inner lavage fluid tube (60).

11. The apparatus of claim 3 wherein said lavage fluid channel (91) is in fluid communication with a suction member.

12. The apparatus of claim 1 wherein said brush adaptor (40, 540) and said inlet adaptor (80) further comprise securing members, said securing members securing said brush adaptor (40, 540) and said inlet adaptor (80) to said top of said reservoir (510).

13. The apparatus of claim 3 wherein a first of said multiple connection tubes connects said reservoir (510) to said inlet channel and a second of said multiple connection tubes connects said reservoir (510) to said lavage fluid channel,
   wherein said pump (520) pumps lavage fluid through a first of said multiple connection tubes and a second of said multiple connection tubes drains lavage fluids from said hollow body (20).

14. An apparatus (10) for cleaning cannulated surgical tools comprising:
   a. a hollow body (20) having a first end, said first end having lavage fluid fluid holes (22) and a second end;
   b. a brush adaptor (40), said brush adaptor (40) being removably affixable to said first end of said hollow body (20);
   c. an inlet adaptor (80) said inlet adaptor (80) being removably affixable to said second end of said hollow body (20);
   d. a lavage fluid connection tube (50) said lavage fluid connection tube (50) having a first end in liquid communication with said first end of said hollow body (20) at said brush adaptor (40) and a second end in liquid communication with said hollow body (20) at said inlet adaptor (80);
   e. an inner lavage fluid tube (60), having an inner channel (64), said inner lavage fluid tube (60) extending within said hollow body (20) and having a distal end in liquid communication through said inner channel with said hollow body (20) and a proximal end in liquid communication through said inner channel with said inlet adaptor (80).

15. An apparatus (10) for cleaning cannulated surgical tools (15) comprising:
   a. a hollow body (20) having
      i. a first end, said first end having lavage fluid holes (22); and
      ii. a second end;

b. a brush adaptor (40, 540), said brush adaptor (40, 540) being removably affixed to said first end of said hollow body (20) and having:
   i. central cavity (41) to receive said first end of said hollow body (20);
   ii. a lavage fluid chamber (43) to receive lavage fluid holes (22);
   iii. a disk cavity (42);
   iv. a disk brush (30) having bristles dimensioned to fit within said disk cavity (42);
   v. an adaptor cover (35) to maintain said disk brush (30) within said disk cavity (42);
   vi. a lavage fluid chamber inlet (44) in liquid communication with said lavage fluid chamber (43) and a lavage fluid connecting tube (50);
c. an inlet adaptor (80), said inlet adaptor (80) having a body (82) with a first surface (81) and a second surface and having:
   i. a body hub (83) extending from said first surface (81) and being dimensioned to receive said hollow body (20), said body hub (83) comprising:
     1. a lavage fluid tube hub (84), extending from said first surface (81) and dimensioned to receive an inner lavage fluid tube (60, 560) and being within liquid communication with said inner lavage fluid tube (60, 560) through a lavage fluid orifice (85); and
     2. lavage fluid openings (86) in fluid communication with said hollow body (20) to enable lavage fluid drainage;
   ii. a lavage fluid hub (90), said lavage fluid hub (90) extending from said second surface of said body hub (83) and being in liquid communication with said tube hub (84) through a lavage fluid inlet channel (92);
   iii. a lavage fluid hub (89), said lavage fluid hub (89) containing a lavage fluid channel (91) in liquid communication with said hollow body (20) and a lavage fluid chamber (94);
   iv. a lavage fluid inlet channel (92) in liquid communication with said lavage fluid tube hub (84);
   v. an upper connecting lavage fluid orifice (87), said upper connecting lavage fluid orifice (87) permitting liquid communication between said lavage fluid connecting tube (50) and said lavage fluid inlet channel (92) and a radial lavage fluid inlet channel (92');
d. a lavage fluid connecting tube (50), said lavage fluid connecting tube (50) having a first end in liquid communication with said first end of said hollow body (20) at said brush adaptor (40, 540) and a second end in liquid communication with said hollow body (20) through said upper connecting lavage fluid orifice (87);
e. an inner lavage fluid tube (60, 560), said inner lavage fluid tube (60, 560) extending within said hollow body (20) and having:
   i. a distal end (61) in liquid communication through an inner channel (64) with said hollow body (20);
   ii. a proximal end (63) in liquid communication through said inner channel (64) with said interior of said inlet adaptor (80);
   iii. a tube brush (70) at said distal end (61); and
   iv. multiple inner spray e openings (62) at said distal end (61).

16. The apparatus of claim 15 further comprising a reservoir (510), said reservoir (510) having:

a. a top, said top having multiple tube receiving areas, and opposing bottom, a pair of opposing sides and a pair of opposing ends;
   b. pump (520) having a power source; and
   c. multiple connection tubes (515', 515", 515"), wherein
     i. a first of said multiple connection tubes (515') connects said reservoir (510) to a second of said multiple connection tubes (515"); and
     ii. said second of said multiple connection tubes (515") connects to a lavage fluid channel (591);
     iii. a third of said multiple connection tubes (515") connects said inlet channel (92, 592) to a lavage fluid tube (560)
   wherein said pump (520) pumps lavage fluid through said multiple connection tubes (515', 515", 515") through said hollow body (20).

17. The apparatus of claim 15 wherein said brush adaptor (40, 540) and said inlet adaptor (80) further comprise securing members, said securing members securing said brush adaptor (40, 540) and said inlet adaptor (80) to said top of said reservoir (510).

18. A method for cleaning cannulated tools using a cleaning apparatus having a hollow body (20) with lavage fluid holes (22) at a first end, a brush adaptor (40) affixed at said first end of said hollow body (20), an inlet adaptor (80) at a second end of said hollow body (20), and an exterior lavage fluid tube (50) having a first end in liquid communication with said hollow body (20) through said brush adaptor (40) and a second end in liquid communication with said hollow body (20) through said inlet adaptor comprising the steps of:
   a. attaching a distal end of a lavage fluid tube from a lavage fluid source to a lavage fluid hub (90) on said inlet adaptor (80);
   b. attaching a distal end of a lavage fluid fluid tube to a lavage fluid hub (91) on said inlet adaptor (80);
   c. attaching a proximal end of an inner lavage fluid tube to said lavage fluid hub (90);
   d. attaching a disk brush (30) having bristles to said brush adaptor (40) opposite said hollow body (20);
   e. attaching a brush (70) to a distal end of said inner lavage fluid tube;
   f. inserting a cannulated tool to be cleaned through said disk brush (30);
   g. inserting said cannulated tool over said brush (70);
   h. causing lavage fluid from said lavage fluid source to enter said lavage fluid hub (90) and enter an inlet channel (92) and into said inner lavage fluid tube;
   i. causing lavage fluid from said inner lavage fluid tube (60) to exit holes (62) and spraying an interior surface of said cannulated tool;
   j. causing lavage fluid to flow to enter said lavage fluid hub (90) and enter a radial lavage fluid inlet channel (92') and flow along a lavage fluid connecting tube (50);
   k. causing lavage fluid to enter said brush adaptor (40) from said lavage fluid connecting tube (50) and exit holes within said brush adaptor (40);
   l. spraying lavage fluid from said holes within said brush adaptor (40) on an exterior of said cannulated tool; and
   m. draining lavage fluid from said hollow body through said lavage fluid hub (91).

19. The method of claim 17 further comprising the step of attaching a suction member to a proximal end of said lavage fluid tube to a suction member and creating a current through said hollow body (20) to lavage fluid any debris removed from said cannulated tool.

20. The method of claim 17 further comprising the steps of:
- a. attaching said cleaning apparatus to a reservoir having a pump;
- b. filling said reservoir with lavage fluid; and
- c. attaching a proximal end of said lavage fluid tube to said reservoir in liquid communication with said lavage fluid.

* * * * *